United States Patent [19]

Burkitt

[11]  4,313,012
[45]  Jan. 26, 1982

[54] PRODUCING ANTHRACENE FROM CREOSOTE

[75] Inventor: David T. Burkitt, Keyport, N.J.

[73] Assignee: Allied Corporation, Morristown, N.J.

[21] Appl. No.: 105,054

[22] Filed: Dec. 19, 1979

[51] Int. Cl.$^3$ .............................................. C10G 21/16
[52] U.S. Cl. .................................................. 585/816
[58] Field of Search ............... 585/804, 812, 807, 808, 585/816, 833, 835, 864, 817, 815, 862; 208/179, 180, 290, 291, 298, 308, 311, 322, 323, 328, 332, 333; 203/43, 46, 54, 62; 568/724, 742, 748, 749

[56] References Cited

U.S. PATENT DOCUMENTS

| 2,011,724 | 10/1932 | Miller | 585/808 |
| 2,052,722 | 10/1932 | Radasch | 585/808 |
| 2,310,500 | 2/1943 | Zavertnik | 208/179 |
| 2,334,667 | 11/1943 | Zavertnik | 208/179 |
| 2,744,059 | 5/1956 | Mayer | 208/179 |

FOREIGN PATENT DOCUMENTS

| 1355733 | 2/1963 | France . | |
| 726860 | 3/1955 | United Kingdom | 585/864 |

OTHER PUBLICATIONS

"Coke and Chemistry"; 1972 (3), pp. 46–47; 1973(3), pp. 32–35; 1973(8), pp. 30–33.
"Kirk–Otamer, Encyclopedia of Chemical Technology"; 1st Ed., vol. 1, pp. 941–943; vol. 7, p. 436; vol. 13, pp. 624–627.
Coke and Chemistry, USSR; 1976(3); pp. 38–42.

Primary Examiner—Frank Sever
Attorney, Agent, or Firm—Alan M. Doernberg

[57] ABSTRACT

Anthracene is precipitated in improved purity and yield by cooling a creosote coal tar distillation fraction. A ketone such as acetone is added to the fraction before the anthracene precipitates. The ketone retains phenanthrene and/or carbazole in the liquid phase as the anthracene precipitates. If the ketone is then removed, the phenanthrene and/or carbazole precipitates and can also be purified.

8 Claims, No Drawings

PRODUCING ANTHRACENE FROM CREOSOTE

BACKGROUND OF THE INVENTION

The present invention relates to the production of anthracene from a middle distillate of coal tar known as creosote.

When the condensate from the destructive distillation of coal (coal tar is distilled, a fraction is produced called "creosote" which is commonly separated into light creosote and heavy creosote, boiling between about 200° C. and about 400° C. Light creosote is generally considered a material having 80 weight % boiling between 235° and 355° C. of which 50–80 weight % boils between 315° and 355° C. The remaining 20 weight % of the total boils higher than 355° C. Heavy creosote is generally considered a material having 50 weight % boiling between 270° and 355° C. and 50 weight % boiling only above 355° C. While creosote is itself useful for wood preserving, several of its components are commonly first recovered because of their higher values for other uses. Anthracene is used in the production of anthraquinone. Phenanthrene and carbazole are sometimes also recovered, generally by purifying by-product streams of anthracene purification.

As described in Kirk-Othmer, *Encyclopedia of Chemical Technology*, Volume 1, Page 942 (1947), anthracene is conventionally produced by cooling a coal tar distillation fraction called "anthracene oil", "green oil" or "light creosote", and leaving it to stand until a precipitate forms called "anthracene salts" or "crude anthracene". The precipitate usually contains 10 to 20 percent anthracene by the method described above; but a 30–40 percent anthracene content can sometimes be obtained by modifications in the selection of a distillate fraction, by cold pressing or by simple washing.

Conventionally, anthracene of greater than about 75 percent purity (usually 90 percent purity or better) is obtained by recrystallizing or leaching crude anthracene. Common solvents for recrystallization include pyridine, furfural, tetrahydrofurfuryl alcohol, chlorobenzene, cyclohexanone, dichlorobenzene, diacetone alcohol and cresylic acid. Common solvents for leaching carbazole and phenanthrene include ammonia, as described, for example, in U.S. Pat. No. 2,011,724 to Miller, and acetone as described by an article of K. A. Belov et al. entitled "Production of Refined Anthracene from Coke-oven Crude" in 1973, Volume 8, *Coke and Chemistry USSR*, pages 30–33. Combinations of leaching and recrystallization are frequently employed to achieve purities of anthracene over 90 percent. Both types of purification steps produce by-product solutions containing phenanthrene and/or carbazole from which these two aromatics can also be recovered.

The conventional techniques for producing anthracene are complex and require multiple steps, first to produce the crude anthracene as a precipitate, and subsequently, to purify anthracene from crude anthracene. Furthermore, when crude anthracene of about 30 percent or higher purity is obtained in order to simplify later purification, much of the anthracene initially present in the creosote distillation fraction is not found in the crude anthracene, but instead remains from the liquid. Analyses of typical commercial operations indicate only about half of the anthracene values in the distillation fraction are recovered in the crude anthracene.

BRIEF DESCRIPTION OF THE INVENTION

The present invention includes an improvement in a process for recovering anthracene as a precipitate from a creosote distillation fraction of coal tar which contains anthracene and either phenanthrene, carbazole or both. The liquid creosote distillation fraction is cooled from a first temperature at which anthracene is in the liquid phase to a second temperature at which anthracene precipitates. The improvement comprises mixing a ketone of 3–6 carbons with the liquid creosote distillation fraction before precipitation of anthracene in an amount of ketone sufficient to retain enough phenanthrene and carbazole in the liquid phase at the second temperature to produce a precipitate at least about 75 weight percent anthracene. It has been found that the addition of ketone enables much more of the anthracene present in the distillation fraction to be found in the initial precipitate while, at the same time, producing a precipitate of higher purity than conventional crude anthracene. In some cases purities of 90 percent or more are reached. These purities are conventionally associated with refined anthracene.

DETAILED DESCRIPTION OF THE INVENTION

The creosote distillation fraction used in the present invention may be produced by a distillation of coal tar. Modern analytical techniques enable the anthracene content of various distillation cuts to be analyzed. Distillation fractions wide enough to include materials of any significant anthracene content are apparently useful in the present invention; nevertheless, because the distillation fraction typically is selected for the ultimate use (e.g. as a wood preservative) of the material after the anthracene is removed, narrower cuts may be selected or, with regard either to the minimum or maximum temperature at which substantial amounts of anthracene are found, one or both may be exceeded if desired. In general, it is preferred that distillation fractions having a major proportion with an atmospheric boiling point between about 255° and about 355° C. be selected, which distillation fraction is normally referred to as "light creosote oil".

After the distillate is condensed, it is mixed with the ketone and cooled to a temperature at which the anthracene precipitates. Since ketone may be introduced relatively cool or even cold, it may serve, in part, to cool the distillate. Means of cooling include external and internal cooling coils and other conventional cooling means. While the ketone may be introduced at any stage in cooling prior to precipitation of anthracene, it is convenient to introduce the ketone before significant cooling of the distillate condensate. Representative temperatures of the condensate at the point where the ketone is introduced are between about 75° and about 125° C.

The preferred ketone for use in the present process is acetone. Acetone is a good solvent for both phenanthrene and carbazole, and therefore prevents precipitation of these two aromatics while the mixture is cooled to a temperature low enough to precipitate most of the anthracene present in the distillate condensate. Acetone is also relatively inert to chemical reaction with materials present in the condensate at temperatures involved. Other ketones of 3–6 carbons can be used such as methylethyl ketone, ethylethyl ketone, methylpropyl ketone, methylbutyl ketone and ethylpropyl ketone. Methylethyl ketone is less preferred than acetone but more preferred than the remainder of these ketones.

Other than temperature, the conditions for mixing the ketone with the distillate condensate are not critical. Superatmospheric pressures may be present, especially if the temperature is sufficiently high to cause a substantial ketone vapor pressure. Mixing or other agitation by conventional means should normally be employed at levels sufficient to prevent precipitation of phenanthrene and carbazole in portions of the distillate which have not been contacted by the ketone.

After mixing the ketone with the distillate condensate, cooling may be continued to temperatures above room temperature (e.g. about 30° C.) to room temperature, or even below room temperature to temperatures such as 0° C. The preferred final temperature is between about −10° C. and about 15° C., more preferably between about −1° C. and about 5° C. In general, the lower the final cooling temperature is, the higher the proportion of anthracene present in the distillate that is recovered in the precipitate. In addition, however, the lower the temperature is, the more impurities are also precipitated, causing the anthracene purity in the precipitate to decrease somewhat as the yield increases. Nevertheless, compared to crude anthracene prepared by precipitating the distillate condensate alone, significantly higher purity of anthracene is present in the precipitate, with substantially the same or better yields of anthracene at any given temperature.

If the anthracene precipitate is relatively pure, such as about 80 percent or greater, it may be used as such for various purposes such as the production of anthraquinone. Mild workup conditions such as washing with acetone, can upgrade material to 80–97 percent purity as indicated in the Examples. If such simple purification techniques are inadequate, however, other schemes such as leaching with ammonia and recrystallization with cyclohexanone or furfural may be employed to upgrade certain precipitates or to achieve certain high purity levels.

After anthracene has been precipitated from the distillate, the liquid phase, now containing the ketone, may be employed to recover phenanthrene and/or carbazole of relatively high purity. The liquid phase is heated and/or subjected to subatmospheric pressures to remove the ketone. Phenanthrene and/or carbazole may then precipitate. If heating has been used to remove the ketone, the remaining liquid may first be cooled to precipate the phenanthrene and/or carbazole. For example, if the creosote (the material from which the anthracene has been removed) is first heated to 150° C. to remove acetone and then cooled to 25° C., a carbazole material will precipitate out. After removing the precipitate from the liquid by conventional techniques such as decantation or filtration, the solids can be redissolved in a minimum amount of acetone at 50° C. and then cooled to less than 20° C. for recrystallization of impurities. The liquid is then removed and heated to 150° C. to remove the acetone. Acetone removed in this and the previous steps may be condensed and then recycled to mix in with the initial creosote distillate fraction. The hot liquid at this point can then be mixed with a solvent in which carbazole is insoluble, for example with toluene, to yield high purity carbazole as a precipitate.

In similar fashion, phenanthrene can be recovered, if desired, from the creosote solids after anthracene has been recovered. The carbazole material that forms after acetone removal and then cooling can be purified by conventional techniques such as recrystallization.

EXAMPLE 1

The creosote oil used in this Example was analyzed by gas chromatography employing a column 183 cm (6 feet) long having a 7.6 cm (3 inch) section at each end filled with methylphenylsilicone and a central section 168 cm (5.5 feet) long filled with a liquid crystalline material known as BMBT (N,N'-bis[p-methoxybenzylidene]-$\alpha,\alpha'$-bi-p-toluidine). The initial column temperature of 150° C. (1 min at initial) was raised at a rateof 4° C./min to 260° C. final (5 min at final). The sample injection port was at 265° C. and a flame ionization detector was at 350° C. The sample of creosote oil was dissolved at about 2–3 weight % in carbon disulfide. Based upon an earlier analysis of crude anthracene and the impurities present therein, tentative identifications were assigned to eleven peaks observed on analysis of the creosote oil. The peaks, in order beginning after carbon disulfide and their approximate area % were:

| Tentative Identification | Area % |
| --- | --- |
| Naphthalene | 14% |
| Methyl naphthalene | 3% |
| Unknown (MW 168 mass spectroscopy) | 4.5% |
| Diphenyl methane | 3.5% |
| Fluorene | 8% |
| Phenanthrene | 20% |
| Anthracene* | 7.6% |
| Methyl anthracene | 3% |
| Carbazole | 4% |
| Fluoranthene & Anthraquinone | 8.5% |
| Pyrene | 6% |
| Total | 82.1% |
| Others | 17.9% |

*this peak may contain a minor impurity eluting with anthracene 150 mL of hot (approximately 100° C.) light creosote oil produced by distilling coal tar were poured into 75 mL of acetone and cooled to −1° C. Gas chromatography analysis of the light creosote oil, before and after this treatment, showed that about 90 percent of the anthracene had been removed from the liquid phase. The cake was slurried with 75 mL of cold (about 5° C.) acetone and filtered. The resulting cake was slurried with 50 mL of cold (about 5° C.) acetone and filtered. This cake was analyzed as being approximately 94.8 percent pure anthracene by weight and represented approximately 56 percent of the initial anthracene in the creosote oil. The solids in the acetone from the second wash contained about 20 percent anthracene while the solids in the acetone from the first wash contained about 2.3 percent anthracene, indicating that the acetone may have been slightly warmer than the optimal temperature for washing the precipitate. The light creosote oil (the liquid phase after the precipitation at −1° C.) had approximately 0.8 percent anthracene compared to 7.64 percent anthracene initially. It should be appreciated that the anthracene present in the acetone used for washing would not be lost in a commercial process because this acetone would be reused in the next wash.

The acetone was then distilled from this creosote at 150° C. and the liquid then cooled to 25° C. where a crystalline precipitate was observed. This precipitate probably contains predominantly phenanthrene and carbazole which can be separated from each other by solvents such as acetone or ethanol in which the carbazole is more soluble.

For example, a sample of this participate was dissolved in about 15 mL of boiling acetone and cooled to 18° C. The solids (presumably crude phenanthrene) were removed and the liquid was boiled to remove the remaining acetone. To the hot liquid, 10 mL of toluene was added. On cooling to room temperature, a solid (crude carbazole) formed. The solid was filtered off, and redissolved in the minimum amount of boiling toluene needed to dissolve it and then cooled to about 30° C. and filtered. The solid (partially purified carbazole) was washed extensively with toluene at room temperature and a white solid resulted. Infrared analysis showed the same spectrum as for a carbazole standard and the gas chromotography results indicated a purity by area percent of about 89 percent.

EXAMPLES 2-5

The same light cresote oil sample used in Example 1 was used for four experiments designed to compare processes with different solvents and second temperatures.

In Example 2, 150 mL of hot light creosote were mixed with 75 mL methanol, and the mixture was cooled to 10° C. and filtered. It was then slurried in 75 mL methanol and again filtered. The resulting cake indicated low purity of anthracene, and thus it was not analyzed.

In Example 3, 150 mL of hot (140° C.) light creosote oil were mixed with 75 mL acetone and then 75 mL water. The mixture was filtered (at about room temperature). The resultant large cake indicated low purity of anthracene.

In Example 4, 150 mL hot light creosote oil were mixed with 75 mL acetone, cooled to 5° C. and filtered. The liquid was heated to 130° C. to drive off the acetone, and then cooled to 50° C. 75 mL of heptane were added, and the mixture was cooled to 10° C. and filtered to give a large cake. The filtrate was heated to 150° C. to drive off the heptane.

In Example 5, 300 mL hot light creosote oil and 150 mL acetone were mixed and cooled slowly to 4.5° C. Samples of liquid were taken over the cooling period and analyzed, showing a gradual decline from 7.6% anthracene to 2.5%. Thus about 33% of the initial anthracene remained in the liquid phase at 5° C. The mixture at 5° C. was filtered and a cake (about 20 g) was recovered containing about 58% of the initial anthracene at a purity by gas chromatography of about 65%. Only 9% was unaccounted for, and this 9% may have remained in the liquid and have been unaccounted for because of non-linearity in the detection of anthracene. The 65% cake was slurried with 75 mL cold acetone (7° C.) and refiltered giving about 13.9 g anthracene of a purity of 97% by gas chromatographic analysis.

A different creosote sample was used for the following two Examples 6 and 7.

EXAMPLE 6

100 mL of light creosote as in Examples 2-5 were heated to 98° C. and mixed with 100 mL acetone and cooled to 7° C. After about one-half hour, the slurry was vacuum filtered and the precipitate was washed with 20 mL of acetone. 1.4 g of material, looking like anthracene of high purity, were obtained.

EXAMPLE 7

150 mL of the light creosote of Example 6 were heated to 98° C. and mixed with 75 mL acetone. The mixture was shaken and cooled to 7° and, after about one-half hour, vacuum filtered. The precipitate was rinsed with 30 mL acetone at room temperature, and 6.9 g dry solids, looking like anthracene of high purity, were obtained.

EXAMPLE 8

150 mL of a third hot light creosote oil having about 6.1-6.2% anthracene were mixed with 75 mL acetone and cooled to 6° C. and filtered. The precipitate was washed twice with room temperature acetone; first 40 mL, then 60 mL. 6.8 g of solids were recovered and analyzed for purity by gas chromatography. The product was about 97% anthracene by area %. The yield was about 59% of theory.

What is claimed is:

1. In a process for recovering anthracene as a precipitate from a creosote distillation fraction of coal tar which contains anthracene and either phenanthrene, carbazole or both, by cooling the liquid creosote distillation fraction from a first temperature at which anthracene is in the liquid phase to a second temperature at which anthracene precipitates; the improvement which comprises mixing a ketone of 3-6 carbons with the liquid creosote distillation fraction before precipitation of anthracene, in an amount of ketone sufficient to retain enough of the phenanthrene and/or carbazole in the liquid phase at the second temperature to produce a precipitate at least about 75 weight percent anthracene and enable recovery of an excess of 50 wt % of the anthracene present in said fraction.

2. The process of claim 1 wherein the ketone is acetone.

3. The process of claim 1 or 2 wherein the precipitate is at least about 90 weight percent anthracene.

4. The process of claim 1 or 2 wherein the second temperature is between about $-10°$ C. and about 15° C.

5. The process of claim 4 wherein the second temperature is between about $-1°$ C. and about 5° C.

6. The process of claim 1 or 2 wherein the anthracene-containing precipitate is removed from the remainder of the creosote distillation fraction and acetone; and then acetone is removed, forming a precipitate containing phenanthrene, carbazole or both.

7. The process of claim 6 wherein carbazole is purified from the precipitate containing phenanthrene, carbazole or both.

8. The process of claim 7 wherein carbazole is purified by dissolving in a limited amount of acetone, separating the liquid from the solid phase and removing carbazole from the liquid phase.

* * * * *